United States Patent
Tayebi

(10) Patent No.: US 7,803,240 B1
(45) Date of Patent: Sep. 28, 2010

(54) METHODS OF REINFORCING MEDICAL BALLOONS AND MAKING REINFORCED MEDICAL BALLOONS AND REINFORCED MEDICAL BALLOONS MADE ACCORDINGLY

(76) Inventor: Amad Tayebi, 5 Sequoia Rd., Westford, MA (US) 01886

( * ) Notice: Subject to any disclaimer, the term of this patent is extended or adjusted under 35 U.S.C. 154(b) by 559 days.

(21) Appl. No.: 11/809,525

(22) Filed: Jun. 1, 2007

Related U.S. Application Data

(60) Provisional application No. 60/809,941, filed on Jun. 1, 2006.

(51) Int. Cl.
*B32B 37/00* (2006.01)
(52) U.S. Cl. .................. 156/149; 156/148; 156/171
(58) Field of Classification Search ................ 156/148, 156/149, 171, 293
See application file for complete search history.

(56) References Cited

U.S. PATENT DOCUMENTS 6,156,254 A * 12/2000 Andrews et al. ............. 264/231
2008/0183132 A1* 7/2008 Davies et al. ........... 604/103.09

\* cited by examiner

*Primary Examiner*—Jeff H Aftergut

(57) ABSTRACT

A method is provided for reinforcing medical balloons in order to withstand high internal pressures without excessive dilation of the reinforced balloon. The method calls for the use of continuous filament high modulus yarns in a braided structure, pressurizing the balloon, inserting the pressurized balloon inside the braided structure, applying axial tension on the braid, thus causing the braided structure to collapse onto and conform to the shape of the pressurized balloon and bonding the reinforcement braid yarns to the exterior surface of the pressurized balloon.

1 Claim, No Drawings

METHODS OF REINFORCING MEDICAL BALLOONS AND MAKING REINFORCED MEDICAL BALLOONS AND REINFORCED MEDICAL BALLOONS MADE ACCORDINGLY

This application claims priority of Provisional Application No. 60/809,941, filed on Jun. 1, 2006 and incorporates, by reference, said Provisional Application in its entirety.

FIELD OF THE INVENTION

The present invention is in the field of medical balloons. In particular, it teaches and claims methods of reinforcing medical balloons and reinforced medical balloons made accordingly which are capable of withstanding high internal pressures without bursting and without excessive dilation (expansion or increasing its dimensions) longitudinally and laterally. More particularly, the balloons made in accordance with the present invention exhibit a low dilation (increase in their dimensions), (lower than 10%), laterally and longitudinally under high internal pressures. As such, the balloons, made in accordance with the present invention, are particularly suitable for use in balloon-tipped catheters where a collapsed wire stent is placed around the collapsed (deflated) balloon, the catheter is threaded through an artery to the location of the blockage. The balloon is then inflated in order to expand the stent surrounding it against the sides of the arterial wall. The balloon is then deflated, leaving the expanded stent in place against the artery wall and the catheter is removed.

BACKGROUND OF THE INVENTION

The prior art teaches and describes a variety of structures, methods and devices for making reinforced balloons for medical applications. Such structures, methods and devices are described in U.S. Pat. Nos. 4,490,421, Re. 33,561, Re. 32,983, 6,156,254, 5,201,706, 5,647,848, 4,706,670, 5,304,340, 5,554,120, 5,868,779, 6,746,425, 6,977,103, 6,190,358, 6,605,057, 6,210,364, and 6,283,939 and pending U.S. Patent Application, Pub. No.: US 2006/0224115, published on Oct. 5, 2006. Each of said U.S. Patents and said pending patent application is incorporated, by reference, in this application in its entirety.

The present invention provides novel simpler structures and methods for making reinforced balloons capable of withstanding high internal pressures without excessive dilation. The present invention also provides a method for selecting the reinforcement braid structures and the reinforcement yarn used for making the reinforcement braid.

In accordance with open literature, jamming is a condition of high fabric packing density where a position of limiting structural geometry is reached due to the inability of solids to inter-penetrate during braid formation. In the case of extensive jamming of a braid it is the point where extension from the pivoting lattice of diamond trellis units stops and extension due to the straining of the strands begins. For compressive jamming it is where strain from similar structural accommodation stops and buckling of the tubular braid starts. Also, the helix angle of a braid is the angle between the helix assumed by the braid element and the axis of the braid.

SUMMARY OF THE INVENTION

In accordance with the present invention, a simple practical method is provided for selecting the reinforcement braid structure and the reinforcement yarn, used for making the reinforcement braid. In accordance with the present invention, virtually, any oriented or non-oriented balloon may be reinforced. Further, in accordance with the present invention, a method is provided wherein the inflated balloon design criteria are specified, including, unreinforced balloon wall thickness, and diameter.

DETAILED DESCRIPTION OF THE INVENTION

In accordance with the present invention, a method is provided for making a reinforced medical balloon, the method comprises the steps of:

providing a monolithic structure balloon, said balloon comprising a balloon body, a proximal shaft, a distal shaft, a proximal transition zone and a distal transition zone, said balloon body having an outer diameter and a wall thickness, a proximal shaft outer diameter and a wall of thickness and a distal shaft outer diameter and a wall thickness, providing a hollow tubular braid made of N reinforcement yarns, said braid being made on a tubular braiding machine utilizing a number of carriers N, a first half of said reinforcement yarns (N/2) forming right hand helices and a second half of said reinforcement yarns (N/2) forming left hand helices, said reinforcement yarns, of said first and said second halves, interlacing in accordance with a predetermined interlacing (weaving/braiding) pattern, said hollow tubular braid having a stress-free (i.e., as produced and laid of a flat surface under no externally applied load) inner diameter, a stress-free helix angle and an axial tension-jammed state inner diameter and an axial compression-jammed state inner diameter, said axial compression-jammed state inner diameter being larger than said outer diameter of said balloon body and said tensile-jammed state inner diameter being not larger than said outer diameter of said distal shaft, said reinforcement yarns having a tensile breaking stress, a tensile modulus, and a slope/tangent of the initial portion of its stress-strain diagram defining the tangent of an angle, said balloon body having a hoop direction breaking stress and a hoop direction modulus and a slope/tangent of the initial portion of its stress-strain diagram defining the tangent of an angle, said balloon body having an axial direction breaking stress and an axial direction modulus and a slope/tangent of the initial portion of its stress-strain diagram defining the tangent of an angle, said tensile breaking stress of said reinforcement yarns being at least 4 gram per denier (70,466 psi) but preferably not exceeding 8 gram per denier (140,932 psi) and said tensile modulus of said reinforcement yarns being in the range of 50 to 95 gram per denier (880,825-1,673,568 psi) and said hoop direction tensile modulus being equal to said tensile modulus of said reinforcement yarns divided by r, where r is the ratio of said tensile modulus of said reinforcement yarns to said hoop direction modulus of said balloon body, said ratio being at least equal to 4.0, inflating said balloon by introducing a pressurized fluid inside said balloon, thereby increasing its bending rigidity and resistance to lateral collapse, sealing the proximal and distal ends of said balloon, inserting said balloon inside said tubular braid, stretching said braid thereby causing it to collapse around said balloon, apply a radially-acting pressure on the exterior surface of the balloon and conform to the shape of said balloon, including said proximal shaft, said proximal transition zone, said balloon body, said distal transition zone and said distal shaft and forming a reinforcement yarn helix angle, in the zone of said body, in the range of 55 to 85 degrees., bonding said stretched braid to exterior surface of said balloon, deflating said balloon, and trimming/cutting said distal and proximal shafts to desired lengths.

The invention claimed is:

1. A method for making a reinforced medical balloon capable of withstanding high internal pressures without bursting and without excessive dilation comprising the steps of:

providing a monolithic structure balloon, said balloon comprising a balloon body, a proximal shaft, a distal shaft, a proximal transition zone and a distal transition zone, said balloon body having an outer diameter b and a wall thickness b, a proximal shaft outer diameter p and a wall of thickness p and a distal shaft outer diameter d and a wall thickness d, providing a hollow tubular braid made of N C reinforcement yarns, said braid being made on a tubular braiding machine utilizing a number of carriers N C, a first half of said reinforcement yarns (N/2) (C) forming right hand helices and a second half of said reinforcement yarns (N/2) (C) forming left hand helices, said reinforcement yarns, of said first and said second halves, interlacing in accordance with a predetermined interlacing pattern, said hollow tubular braid having a stress-free inner diameter sf, and an axial tension-jammed state inner diameter jt and an axial compression-jammed state inner diameter jc, said axial compression-jammed state inner diameter jc being larger than said outer diameter of said balloon body b and said tensile jammed state inner diameter jt being not larger than said outer diameter of said distal shaft d, said reinforcement yarns having a tensile breaking stress r, and a tensile modulus r, said balloon body having a hoop direction breaking stress h and a hoop direction modulus h, said r tensile breaking stress of said reinforcement yarns being at least 4 gram per denier (70,466 psi) but not exceeding 8 gram per denier (140,932 psi) and said r tensile modulus of said reinforcement yarns being in the range of 50 to 95 gram per denier (880,825-1,673,568 psi) and said hoop direction modulus of said balloon body h being equal to said tensile modulus of said reinforcement yarns divided by r, r where r is the ratio of said tensile modulus of said reinforcement yarns to said hoop direction modulus of said balloon body r/h, said ratio being at least equal to 4.0, inflating said balloon by introducing a pressurized fluid inside said balloon, thereby increasing its bending rigidity and resistance to lateral collapse, sealing the proximal and distal ends of said balloon, inserting said balloon inside said tubular braid, stretching said braid thereby causing it to collapse around said balloon, apply a radially-acting pressure on the exterior surface of the balloon and conform to the shape of said balloon, including said proximal shaft, said proximal transition zone, said balloon body, said distal transition zone and said distal shaft and forming a reinforcement yarn helix angle, in the zone of said body, in the range of 55 to 85 degrees, bonding said stretched braid to exterior surface of said balloon, deflating said balloon, and trimming/cutting said distal and proximal shafts to desired lengths.

* * * * *